(12) United States Patent
Goble et al.

(10) Patent No.: US 7,963,984 B2
(45) Date of Patent: Jun. 21, 2011

(54) APPARATUS AND METHOD FOR ATTACHING A GRAFT LIGAMENT TO A BONE

(75) Inventors: E. Marlowe Goble, Alta, WY (US); T. Wade Fallin, Hyde Park, UT (US); Kenneth J. Gardner, Smithfield, UT (US)

(73) Assignee: Stryker Ortho Pedics, Mahwah, NJ (US)

( * ) Notice: Subject to any disclaimer, the term of this patent is extended or adjusted under 35 U.S.C. 154(b) by 346 days.

(21) Appl. No.: 11/760,461

(22) Filed: Jun. 8, 2007

(65) Prior Publication Data
US 2008/0140197 A1    Jun. 12, 2008

Related U.S. Application Data

(60) Continuation of application No. 10/383,179, filed on Mar. 6, 2003, now Pat. No. 7,229,448, which is a division of application No. 09/837,594, filed on Apr. 18, 2001, now Pat. No. 6,620,195.

(51) Int. Cl.
*A61B 17/04* (2006.01)
*A61B 17/86* (2006.01)
*A61F 2/08* (2006.01)

(52) U.S. Cl. ........ 606/321; 606/98; 606/328; 623/13.14
(58) Field of Classification Search .................. 606/98, 606/321; 623/13.14
See application file for complete search history.

(56) References Cited

U.S. PATENT DOCUMENTS

| | | | |
|---|---|---|---|
| 2,347,567 A * | 4/1944 | Kresse | 424/487 |
| 3,579,831 A | 5/1971 | Stevens et al. | |
| 5,431,651 A | 7/1995 | Goble | |
| 5,542,847 A | 8/1996 | Margulies | |
| 5,890,902 A | 4/1999 | Sapian | |
| 5,891,150 A | 4/1999 | Chan | |
| 6,214,012 B1 * | 4/2001 | Karpman et al. | 606/93 |

* cited by examiner

Primary Examiner — Eduardo C Robert
Assistant Examiner — Andrew Yang
(74) Attorney, Agent, or Firm — Peter K. Johnson; James L. Larson; G. Jo Hays

(57) ABSTRACT

A novel fixation system for fixing a graft ligament in a bone tunnel. The fixation system comprises an interference screw comprising a body having a distal end and a proximal end, screw threads extending longitudinally along the body, and a transversely-extending region formed in the body for receiving a transverse pin therein, whereby to securely lock the interference screw, and hence the graft ligament, to the bone. In accordance with a further feature of the present invention, there is provided a method for attaching a graft ligament to a bone, the method comprising the steps of: (i) drilling a tunnel in the bone; (ii) positioning the graft ligament in the bone tunnel; (iii) placing an interference screw in the bone tunnel so as to force the graft ligament laterally against the opposite side of the bone tunnel; and (iv) advancing a transverse pin transversely through the bone and through the interference screw so as to securely lock the interference screw, and hence the graft ligament, to the bone. The present invention can also be applied to attach other objects to bone, e.g., a bone fragment to bone.

14 Claims, 16 Drawing Sheets

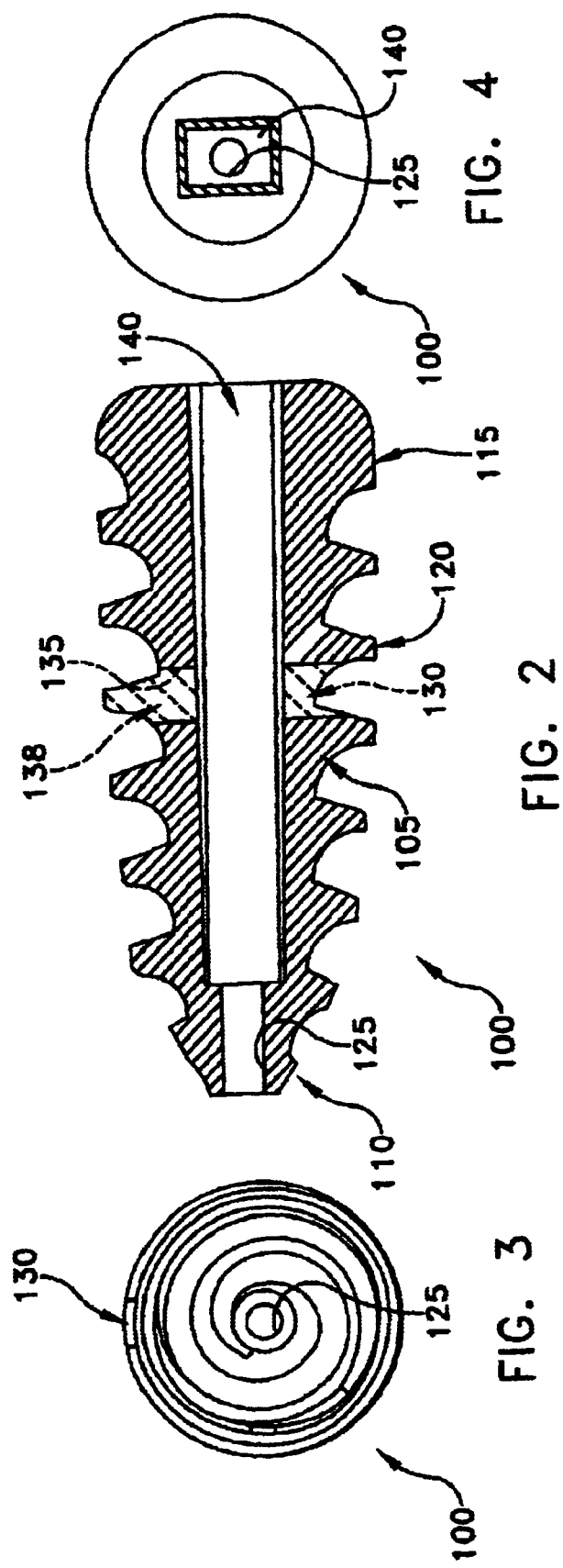

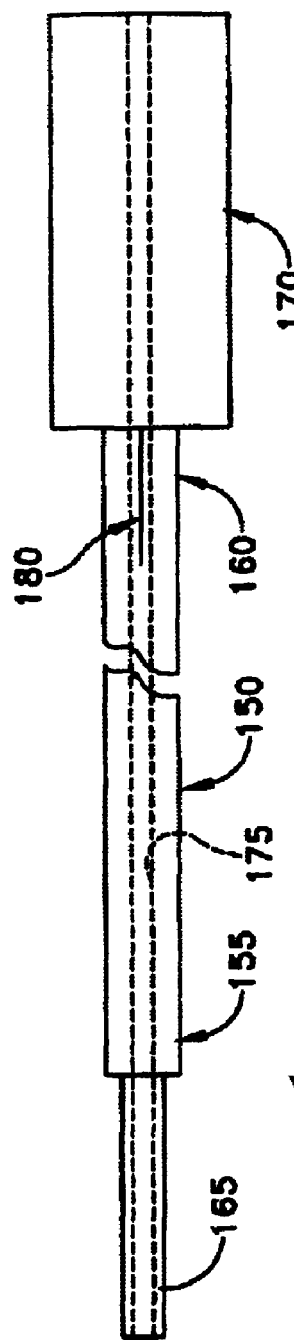
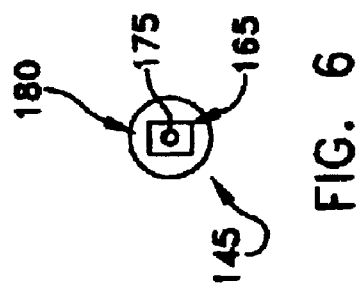
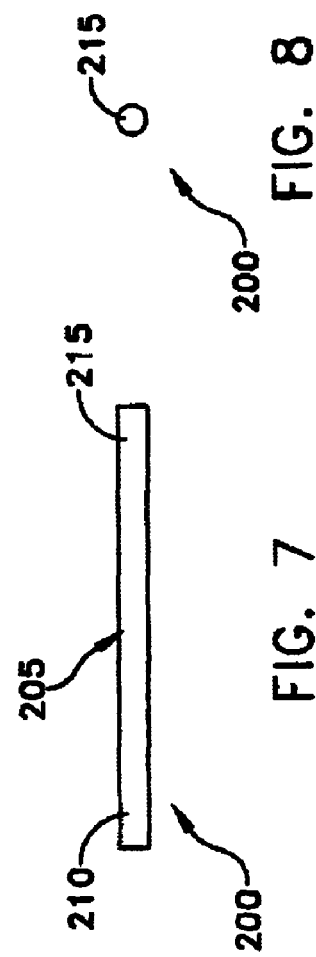

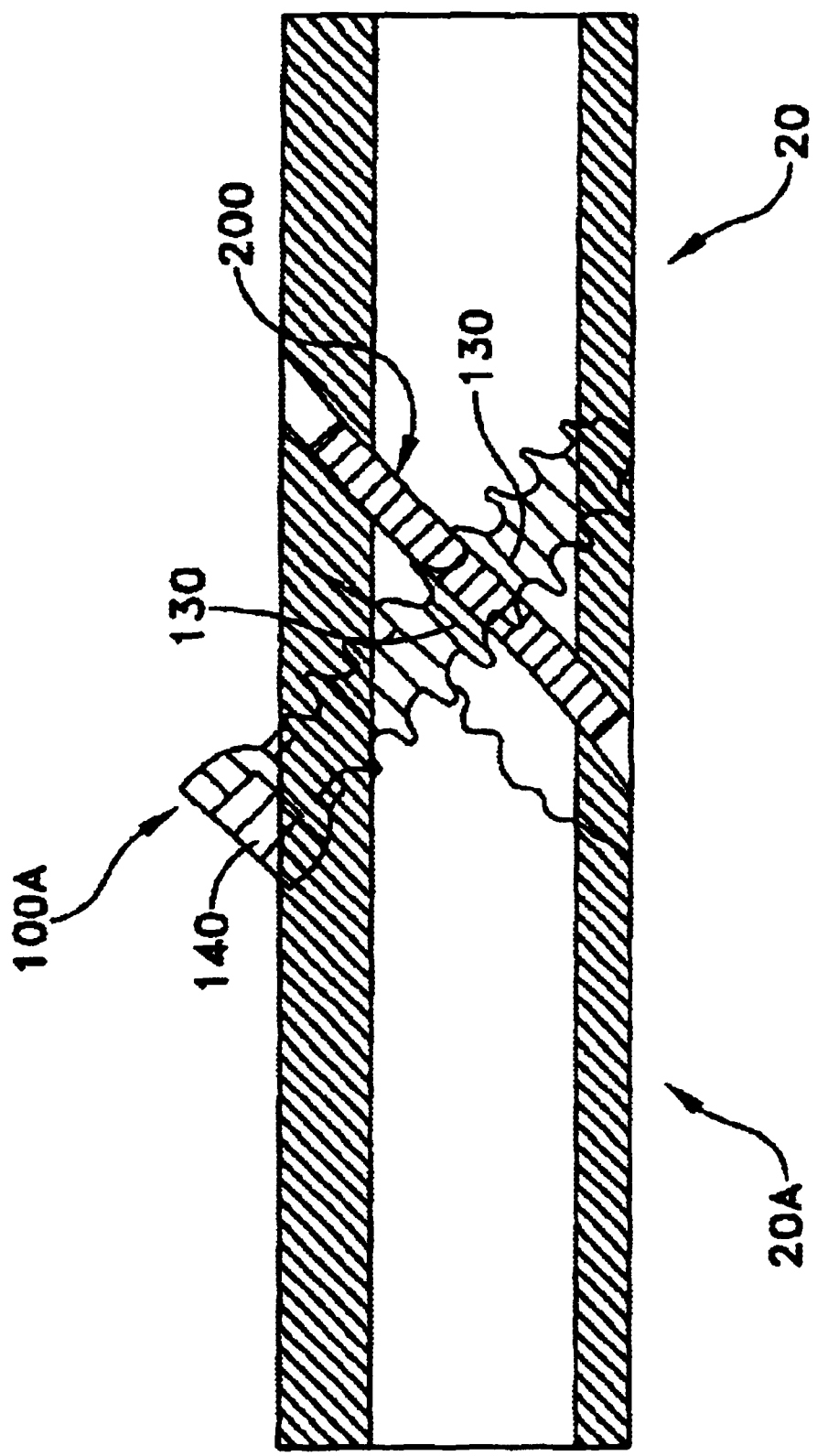

APPARATUS AND METHOD FOR ATTACHING A GRAFT LIGAMENT TO A BONE

CROSS-REFERENCE TO RELATED APPLICATIONS

This application is a continuation of:

Pending prior U.S. application Ser. No. 10/383,179, filed Mar. 6, 2003 by E. Marlowe Goble, et al. for APPARATNS AND METHOD FOR ATTACHING A GRAFT LIGAMENT TO A BONE, soon to issue as U.S. Pat. No. 7,229,448, which is a divisional of:

Prior U.S. application Ser. No. 09/837,594, filed Apr. 18, 2001 by E. Marlowe Goble, et al., for APPARATUS AND METHOD FOR ATTACHING A GRAFT LIGAMENT TO A BONE, now U.S. Pat. No. 6,620,195.

All of the foregoing are incorporated herein by reference.

BACKGROUND OF THE INVENTION

1. The Field of the Invention

The present invention relates to surgical apparatus and methods in general, and more particularly to apparatus and methods for attaching a graft ligament to a bone.

2. The Relevant Technology

In the human knee, the anterior cruciate ligament (i.e., the ACL) extends between the top end of the tibia and the bottom end of the femur. This ligament plays an important role in providing both static and dynamic stability to the knee. Often, the ACL is ruptured or torn as the result of, for example, a sports-related injury. Consequently, various surgical procedures have been developed for reconstructing the ACL so as to restore normal function to the knee.

For example, the ACL may be reconstructed by replacing the damaged ACL with a synthetic or harvested graft ligament. More particularly, with such a procedure, bone tunnels are typically formed in the top end of the tibia and the bottom end of the femur, with one end of the graft ligament being positioned in the femoral tunnel and the other end of the graft ligament being positioned in the tibial tunnel. The two ends of the graft ligament are anchored in place in various ways well known in the art so that the graft ligament thereafter extends between the tibia and the femur in substantially the same way, and with substantially the same function, as the original ACL In some circumstances, a graft ligament harvested from the body may include a bone block connected to one or both of its ends. For example, a portion of a patella tendon, with a portion of the patella still attached, may be harvested from the patient so as to provide the graft ligament. The graft ligament's bone block (i.e., the patella block) can facilitate integration of the graft ligament with the patient's host bone, due to the rapid integration of bone with bone.

In other circumstances, a graft ligament harvested from the body may consist entirely of soft tissue. For example, a portion of the hamstring tendon may be harvested from the patient so as to provide the graft ligament. In this case, only the soft tissue is available to integrate with the host bone.

In one well-known procedure, the graft ligament is placed in the bone tunnel and then a fixed in place using a headless orthopedic screw, generally known as an "interference" (or "Kurosaka") screw. More particularly, with this procedure, the graft ligament is placed in the bone tunnel and then an interference screw is advanced into the bone tunnel so that the screw extends parallel to the bone tunnel and simultaneously engages both the graft ligament and the host bone. The interference screw essentially drives the graft ligament laterally, into engagement with the opposite side of the bone tunnel, whereby to secure the graft ligament to the host bone.

Interference screws work well in many circumstances. Unfortunately, however, interference screws do not work perfectly in all clinical situations. For example, interference screws can have limited effectiveness where bone quality is poor. This can be particularly true in the tibia. In fact, in some circumstances, the bone quality in the tibia can be sufficiently poor that a surgeon will avoid the use of an interference screw altogether and uses some alternative form of ligament fixation. Unfortunately, however, such alternative forms of ligament fixation generally suffer from significant deficiencies of their own.

In addition to the foregoing, other objects frequently need to be attached to bone as well. For example, in the area of fracture fixation, bone fragments need to be re-attached to bone. Current attachment techniques typically rely on the use of bone screws and the like to effect re-attachment. However, bone screws typically only provide a single point of purchase with the bone and can provide less than optimal stability, frequently requiring the use of additional screws, etc.

SUMMARY OF THE INVENTION

Accordingly, a primary object of the present invention is to provide improved apparatus for attaching a graft ligament to a bone.

Another object of the present invention is to provide improved apparatus for attaching an object to bone.

And another object of the present invention is to provide an improved method for attaching a graft ligament to a bone.

Still another object of the present invention is to provide an improved method for attaching an object to bone.

These and other objects of the present invention are addressed by the provision and use of a novel fixation system for fixing a graft ligament in a bone tunnel, wherein the fixation system comprises an interference screw comprising a body having a distal end and a proximal end, screw threads extending longitudinally along the body, and a transversely-extending region formed in the body for receiving a transverse pin therein, whereby to securely lock the interference screw, and hence the graft ligament, to the bone.

In accordance with a further feature of the present invention, the transversely-extending region formed in the body of the interference screw may comprise a hole formed in the body of the interference screw.

And in accordance with a further feature of the present invention, the proximal end of the body of the interference screw has a keyway formed therein so as to permit (i) driving of the interference screw, and (ii) association with a transverse guide assembly for placing a transverse pin through the host bone and through the transversely-extending region formed in the interference screw, whereby to securely lock the interference screw, and hence the graft ligament, to the bone.

And in accordance with a further feature of the present invention, there is provided a novel transverse guide assembly for use in passing the transverse pin through the host bone and through the transversely-extending region formed in the interference screw, wherein the transverse guide assembly comprises a key member, a boom member and a guide member, and further wherein the key member is adapted to be connected to the keyway formed in the proximal end of the interference screw, the boom member is connected to the key member and supports the guide member outboard of the interference screw, and the guide member is adapted to support a drill for forming a hole to receive the transverse pin which extends transversely through the host bone and the transversely-extending region formed in the interference screw.

In accordance with a further feature of the present invention, there is provided a method for attaching a graft ligament to a bone, the method comprising the steps of: (i) drilling a tunnel in the bone; (ii) positioning the graft ligament in the bone tunnel; (iii) placing an interference screw in the bone tunnel so as to force the graft ligament laterally against the opposite side of the bone tunnel; and (iv) advancing a transverse pin transversely through the bone and through the interference screw so as to lock the interference screw, and hence the graft ligament, to the bone.

The present invention can also be applied to attach other objects to bone, e.g., a bone fragment to a bone.

BRIEF DESCRIPTION OF THE DRAWINGS

These and other objects and features of the present invention will be more fully disclosed in, or rendered obvious by, the following detailed description of the preferred embodiments of the invention, which is to be considered together with the accompanying drawings wherein like numbers refer to like parts, and further wherein:

FIG. 2 is a side elevational view of a novel interference screw formed in accordance with the present invention;

FIG. 3 is an end view showing the distal end of the interference screw shown in FIG. 2;

FIG. 4 is an end view showing the proximal end of the interference screw shown in FIG. 2;

FIG. 5 is a side elevational view of a driver which may be used to set the interference screw shown in FIG. 2;

FIG. 6 is an end view showing the distal end of the driver shown in FIG. 5;

FIG. 7 is side elevational view of a transverse pin which may be used in connection with the present invention;

FIG. 8 is an end view showing the proximal end of the transverse pin shown in FIG.

FIG. 22 is a schematic view illustrating a novel form of fracture fixation utilizing the present invention.

DETAILED DESCRIPTION OF THE PREFERRED EMBODIMENTS

Figure 1:
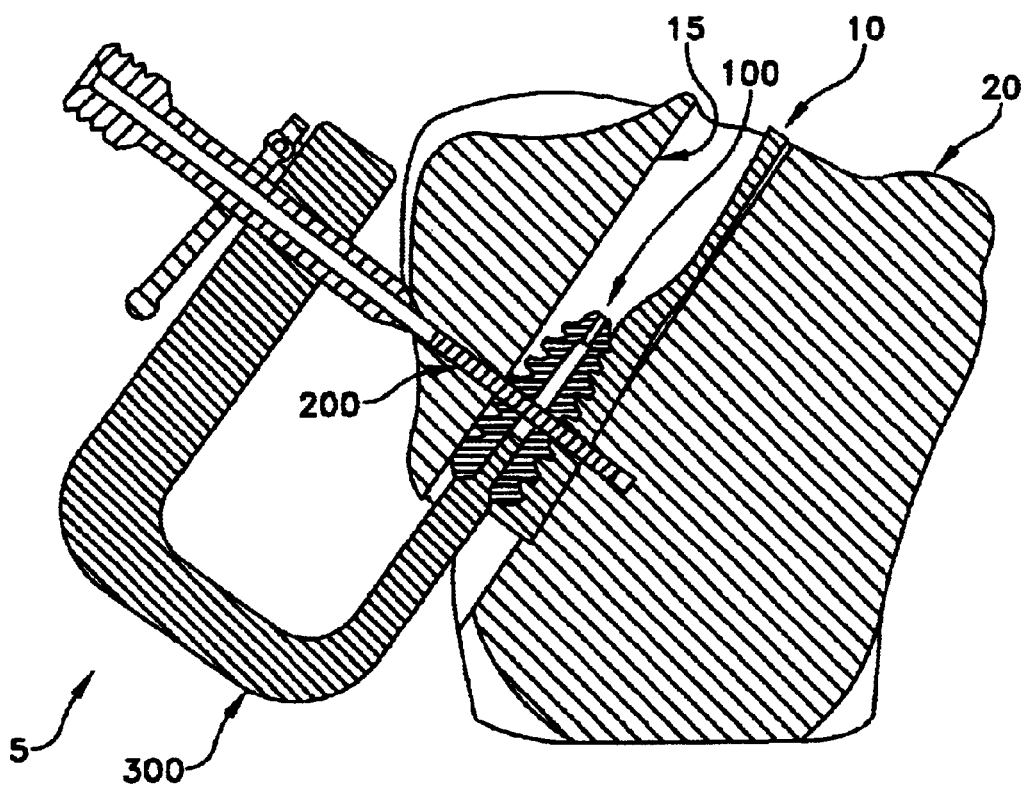
FIG. 1 is a side elevational view, partially in section, showing a novel fixation system attaching a graft ligament to a bone.

Referring first to FIG. 1, there is shown a novel fixation system 5 for securing a graft ligament 10 within a bone tunnel 15 of a tibia 20 of a human knee joint.

Novel fixation system 5 generally comprises an interference screw 100, a transverse pin 200 and a transverse guide assembly 300.

Interference screw 100 is shown in greater detail in FIGS. 2-4. Interference screw 100 generally comprises a body 105 having a distal end 110 and a proximal end 115. Screw threads 120 extend longitudinally along body 105. Preferably screw threads 120 extend along the entire length of the screw, from distal end 110 to proximal end 115; however, if desired, screw threads 120 may extend along only a portion of the length of the body. Interference screw 100 is preferably cannulated, with a central lumen 125 extending along its length, whereby the interference screw may be delivered to a surgical site over a guidewire if desired.

Interference screw 100 has a transversely-extending region 130 formed in body 105 for receiving transverse pin 200 therein, as will hereinafter be discussed in further detail. Where interference screw 100 is formed out of a relatively permanent material, e.g., metal or plastic, transversely-extending region 130 comprises an opening 135 formed in body 105, and this opening 135 may or may not be filled with a bioabsorbable material 138 if desired. Where interference screw 100 is formed entirely out of a bioabsorbable material, transversely-extending region 130 may, but need not, comprise such opening 135.

The proximal end 115 of body 105 includes a keyway 140 to permit (i) driving of the interference screw, and (ii) association with transverse guide assembly 300 for placing transverse pin 200 through the host bone (e.g., tibia 20) and through transversely-extending region 130 formed in body 105, whereby to lock the interference screw to the bone. Keyway 140 has a non-circular configuration (e.g., rectangular or ovoid, etc.) and a fixed angular orientation relative to transversely-extending region 130 (e.g., aligned). This construction is important, since it allows the particular angular orientation of transversely-extending region 130 to be determined from the angular orientation of keyway 140, as will hereinafter be discussed in further detail.

Looking next at FIGS. 5 and 6, there is shown a driver 145 which may be used to set interference screw 100. Driver 145 generally comprises a shaft 150 having a distal end 155 and a proximal end 160. Distal end 155 includes a key projection 165 extending distally from shaft 150. Key projection 165 is sized so as to be received within keyway 140 of interference screw 100, whereby interference screw 100 can be turned by shaft 150. A handle 170 is attached to the proximal end of shaft 150. Driver 145 is preferably cannulated, with a central lumen 175 extending along its length, whereby driver 145 may be used in conjunction with a guidewire if desired.

Shaft 150 of driver 145 preferably has an orientation marking 180 formed thereon. Orientation marking 180 has a fixed angular orientation relative to key projection 165. This construction is important, since it allows the particular angular orientation of key projection 165 (and, by extension, an interference screw 100 mounted to key projection 165) to be determined by the angular orientation of orientation marking 180, as will hereinafter be discussed in further detail.

Looking now at FIGS. 7 and 8, transverse pin 200 comprises an elongated shaft 205 having a distal end 210 and a proximal end 215. Transverse pin 200 may be formed out of a relatively permanent material, e.g., metal or plastic, or a bioabsorbable material, e.g., PLA, PGA, etc. Transverse pin 200 is sized so as to be received within transversely-extending region 130 formed in body 105 of interference screw 100, as will hereinafter be discussed in further detail.

If desired, transverse pin 200 may be smooth, ribbed, threaded, etc., and may be headed or headless. If threaded, the threads may extend along the entire length of the shaft or only a portion thereof (e.g., along only the proximal end of shaft 205).

Figure 9:
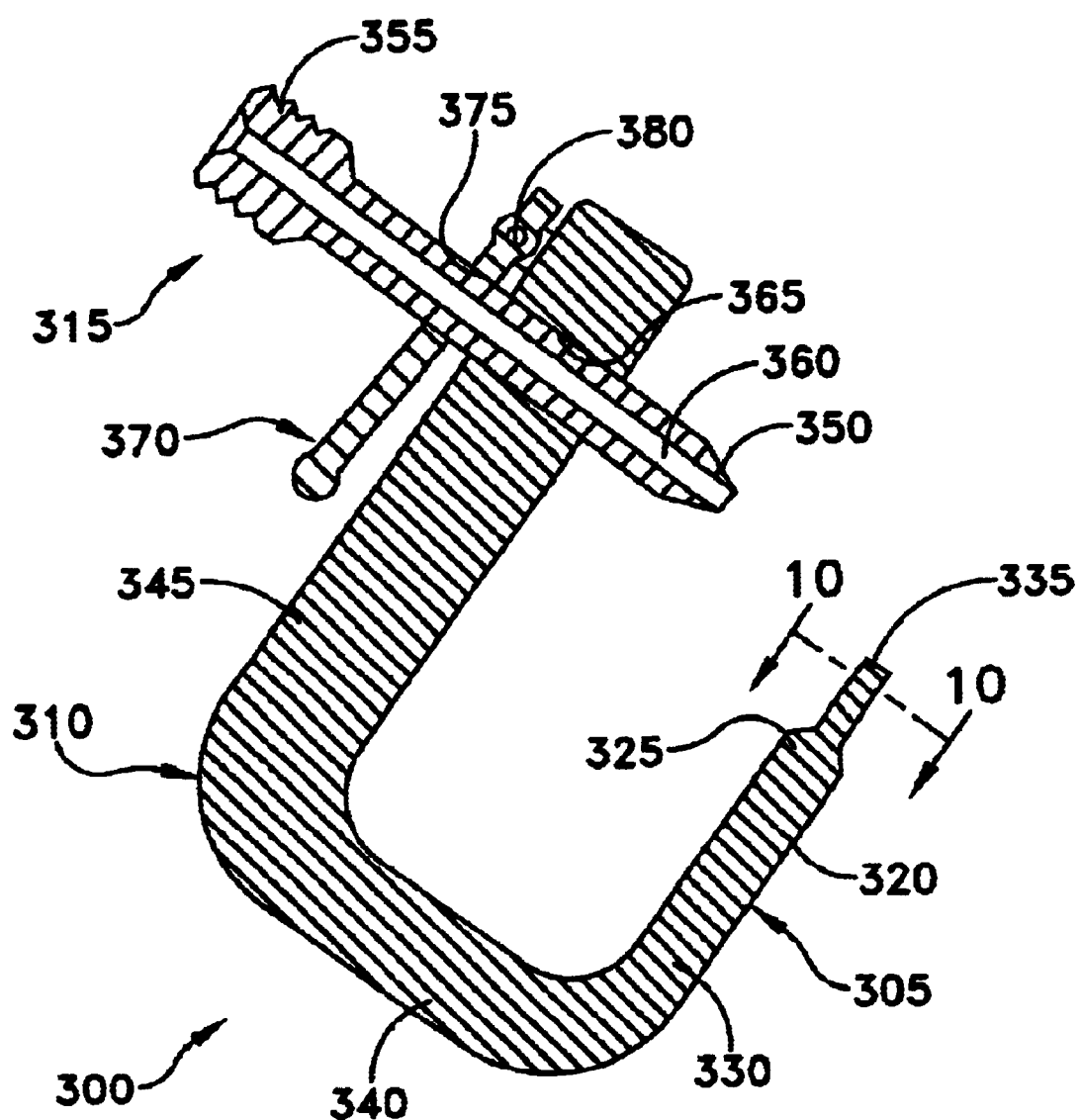
FIG. 9 is a side elevational view of a transverse guide assembly formed in accordance with the present invention.
Figure 10:
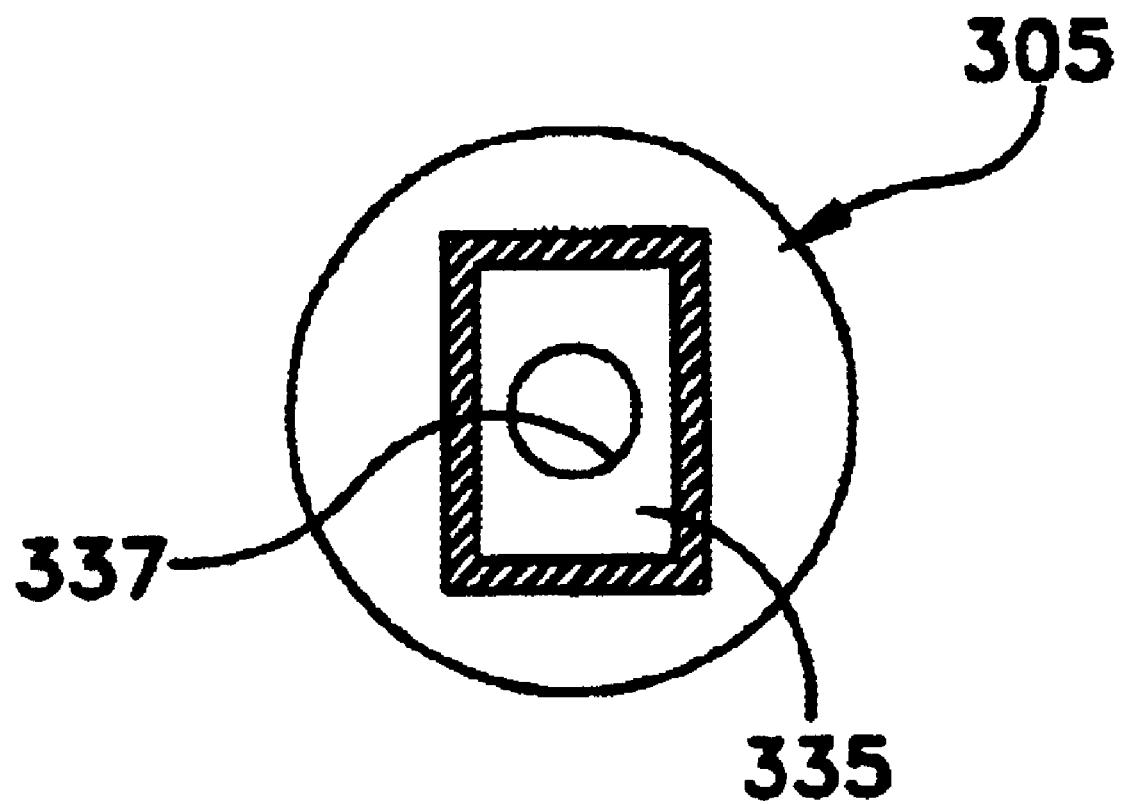
FIG. 10 is a sectional view taken along line 10-10 of FIG. 9.

Looking next at FIGS. 9 and 10, transverse guide assembly 300 includes a key member 305, a boom member 310, and a guide member 315.

Key member 305 comprises an elongated body 320 having a distal end 325 and a proximal end 330. Distal end 325 includes a key projection 335 extending distally from body 320. Key projection 335 is sized so as to be received within keyway 140 of interference screw 100, as will hereinafter be discussed in further detail. Elongated body 320 of key member 305 is preferably cannulated, with a central lumen 337 (FIG. 10) extending along its length, whereby transverse guide assembly 300 may be advanced to a surgical site over a guidewire if desired.

Boom member 310 has a first portion 340 for connection to key member 305, and a second portion 345 for connection to guide member 315. If desired, first portion 340 may be permanently attached to key member 305, e.g., as shown in FIG. 9; alternatively, it may be selectively detachable from key member 305.

Guide member 315 has a distal end 350 and a proximal end 355. Guide member 315 is cannulated, with a central lumen 360 extending from distal end 350 to proximal end 355. Lumen 360 is sized so as to accommodate a drill bit and, thereafter, a transverse pin 200 therein, A as will hereinafter be described in further detail.

Guide member 315 is attached to second portion 345 of boom member 310. More particularly, guide member 315 may be permanently attached to second portion 345 if desired or, more preferably, it may be slidably mounted to second portion 345 by passing guide member 315 through a bore 365 formed in second portion 345. Where guide member 315 is slidingly mounted to second portion 345 by passing guide member 315 through a bore 365 in second portion 345, guide member 315 may be selectively locked to second portion 345 by a spring-biased pivot lever 370. More particularly, spring-biased pivot lever 370 includes a center hole 375 which receives guide member 315 therein; when the free end of pivot lever 370 is pressed toward second portion 345, against the bias of a spring 380, center hole 375 will be aligned with guide member 315 and guide member 315 will be free to move relative to second portion 345; but when the free end of pivot lever 370 is released, so that spring 380 moves the free end of pivot lever away from second portion 345, center hole 375 will move out of alignment with guide member 315 and guide member 315 will be locked relative to second portion 345.

Regardless of how guide member 315 is attached to boom member 310, guide member 315 is attached so as to have a fixed angular orientation relative to key projection 335 of key member 305. This construction is important, since it allows the particular angular orientation of guide member 315 to be determined by the angular orientation of key projection 335 of key member 305, as will hereinafter be discussed in further detail.

Figure 11:
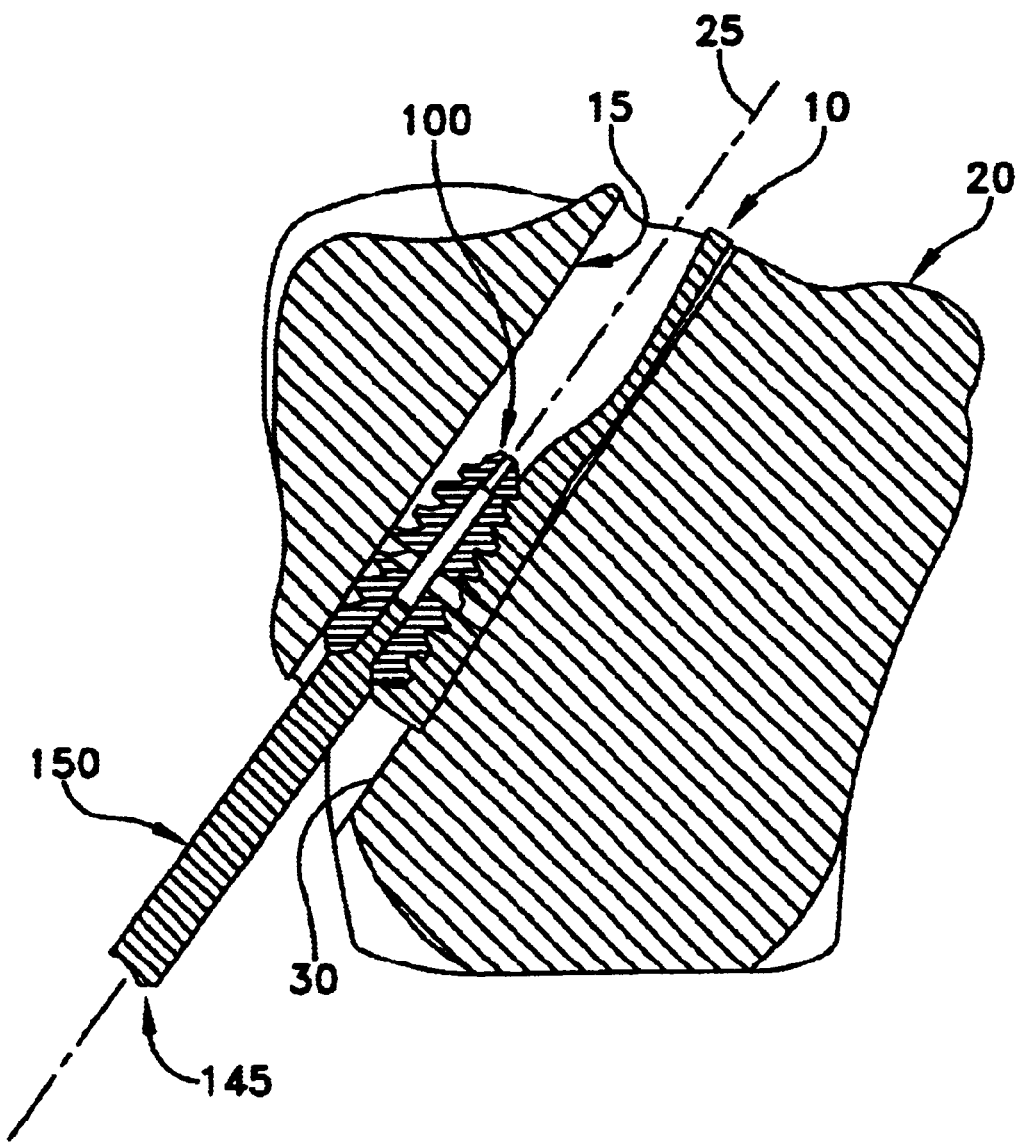
FIGS. 11-14 are side elevational views, partially in section, showing various steps in attaching a graft ligament to a bone.

Fixation system 5 may be used to attach a graft ligament to a bone. More particularly, and looking now at FIG. 11, bone tunnel 15 is formed in bone 20, and graft ligament 10 is positioned within the bone tunnel. Then interference screw 100 is mounted on driver 145 and advanced (preferably over a guidewire 25) into bone tunnel 15 until the interference screw engages both graft ligament 10 and bone 20. Interference screw 100 essentially drives graft ligament 10 laterally, into engagement with the opposite side 30 of bone tunnel 15, whereby to press the graft ligament against bone 20. As driver 145 is turned, its orientation marking 180 can be observed, whereby to determine the angular orientation of interference screw 100. After interference screw 100 has been properly set, driver 145 is removed.

Figure 12:
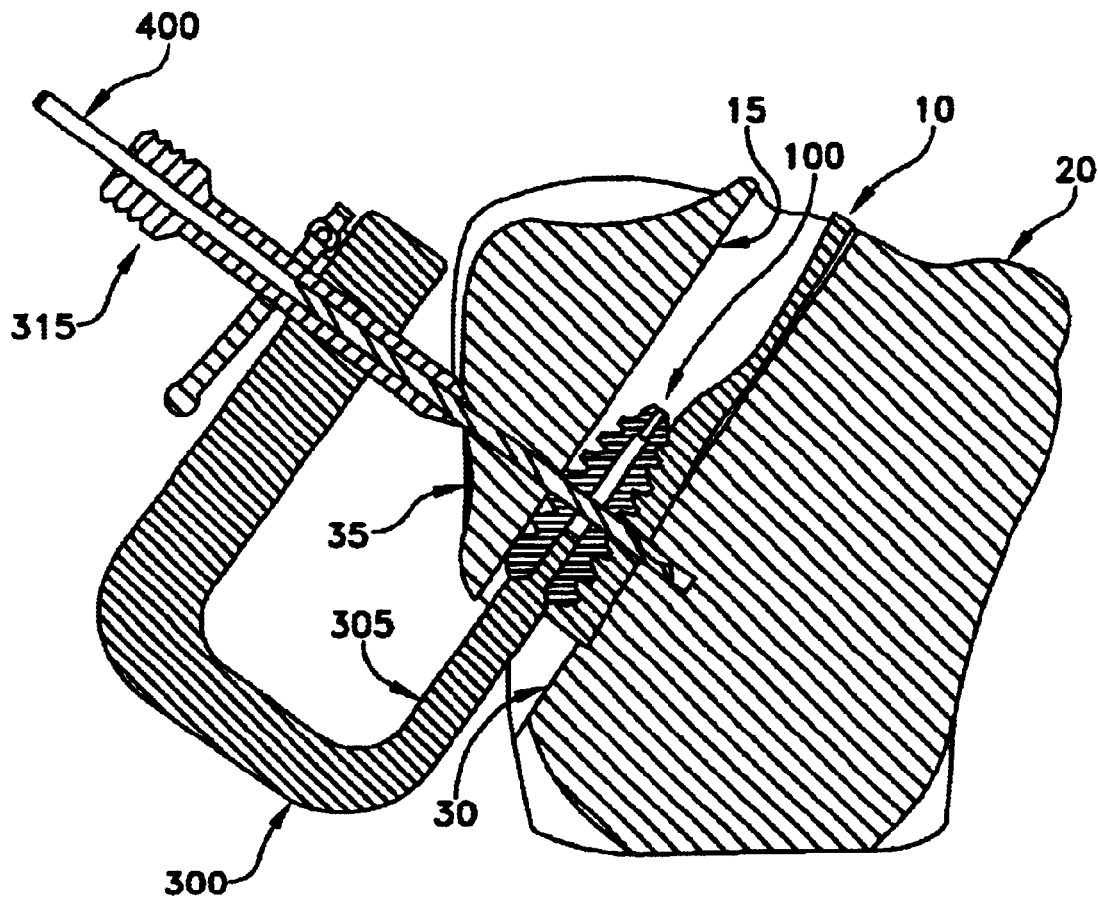

Next, and looking now at FIG. 12, transverse guide assembly 300, with its guide member 315 fit loosely to boom member 310, has its key member 305 advanced toward interference screw 100. Key projection 335 is fit into keyway 140 formed in the proximal end of interference screw 100; as this occurs, guide member 315 of transverse guide assembly 300 will be automatically aligned with the transversely-extending region 130 formed in body 105 of interference screw 100. In this respect it will be recalled that where interference screw 100 comprises a substantially permanent material, transversely-extending region 130 comprises an opening 135 in body 105 (which opening 135 may or may not be filled with a bioabsorbable material 140 if desired), and guide member 315 will be aligned with this opening 135.

Then, where guide member 315 is movable relative to boom member 310, guide member 315 is advanced until its distal end 350 engages the outer surface 35 of bone 20. This helps secure transverse guide assembly 300 relative to bone 20.

Figure 13:
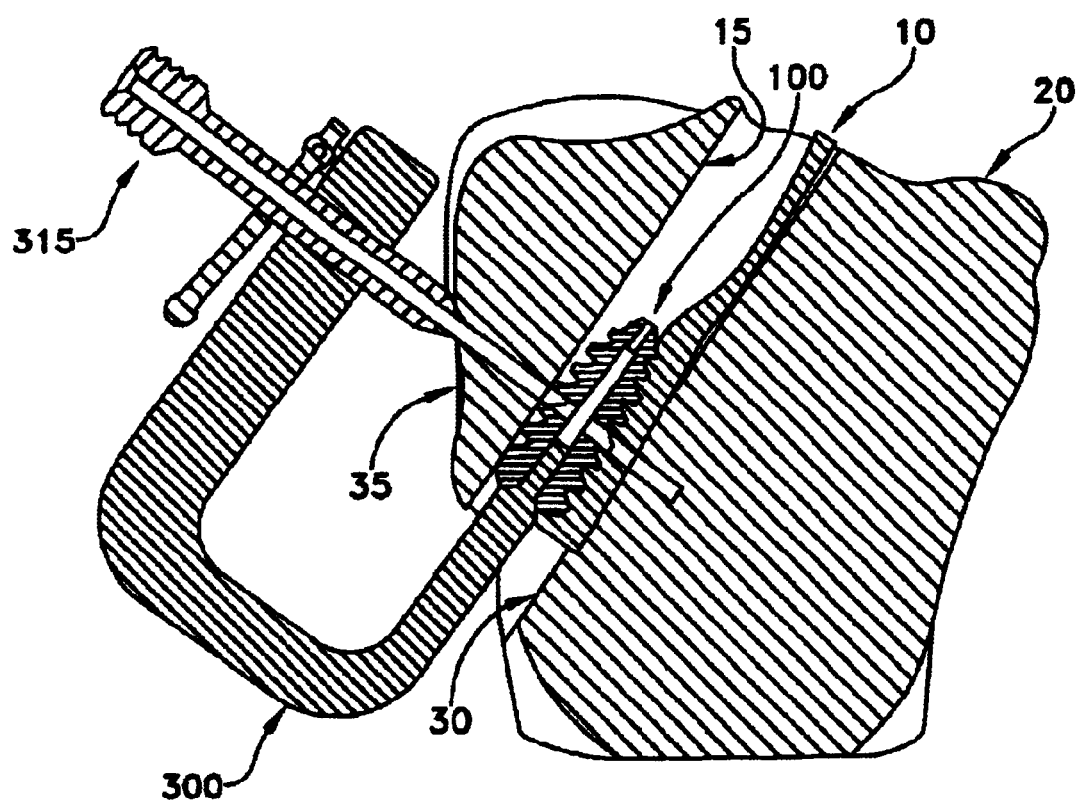
Figure 14:
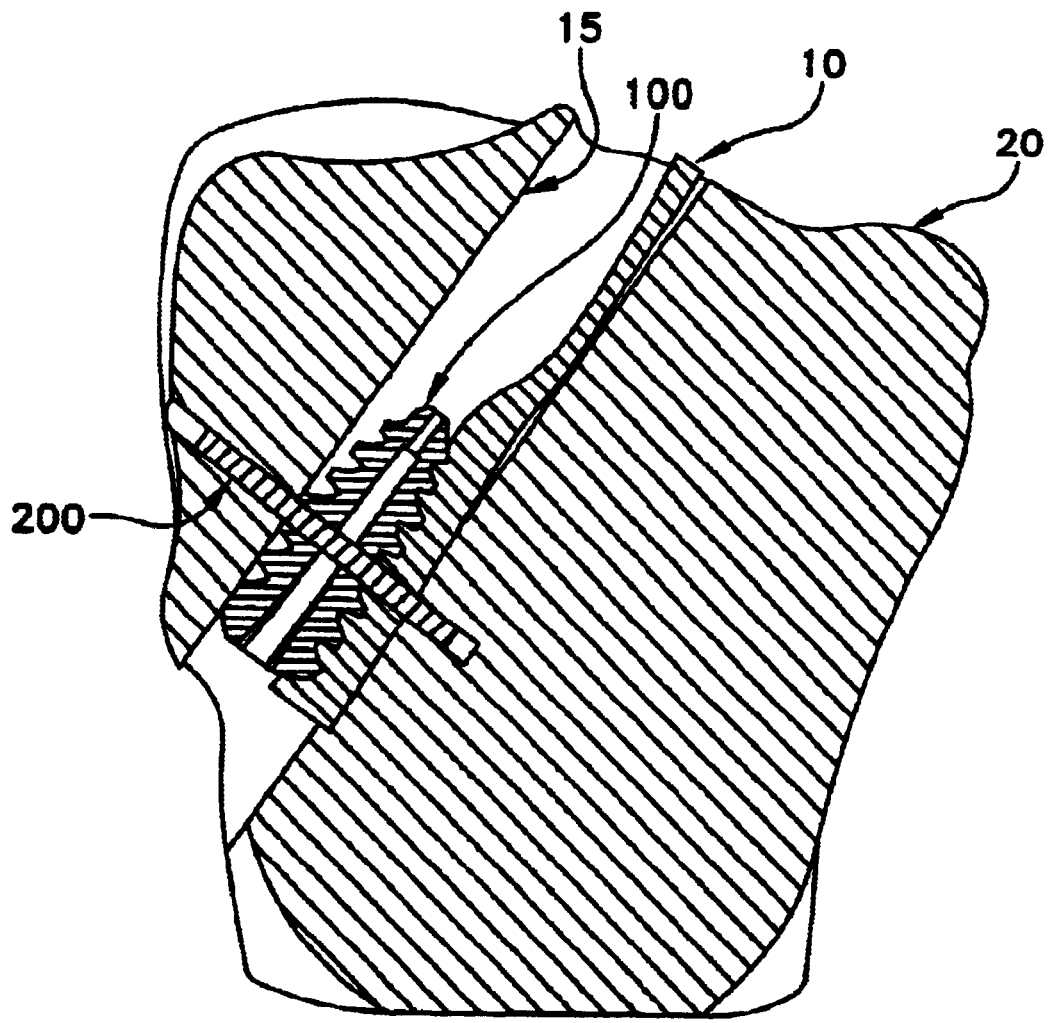

Next, a drill 400 (FIG. 12) is advanced through the central lumen 360 of guide member 315. Drill 400 is used to drill transversely through bone 20, bone tunnel 15, any bioabsorbable material 140 located in the transversely-extending region 130 formed in interference screw 100, and into the bone on the opposite side 30 of the bone tunnel. Drill 400 may also pass through graft ligament 10, depending on the angular disposition of guide member 315 and the size of graft ligament 10. Then drill 400 is withdrawn (FIG. 13), and transverse pin 200 is advanced through the central lumen 360 of guide member 315 (FIG. 1). Transverse pin 200 is passed through bone 20, across interference screw 100, and back into bone 20. Then transverse guide assembly 300 is withdrawn (FIG. 14), leaving interference screw 100, and hence graft ligament 10, securely locked to bone 20.

Figure 15:
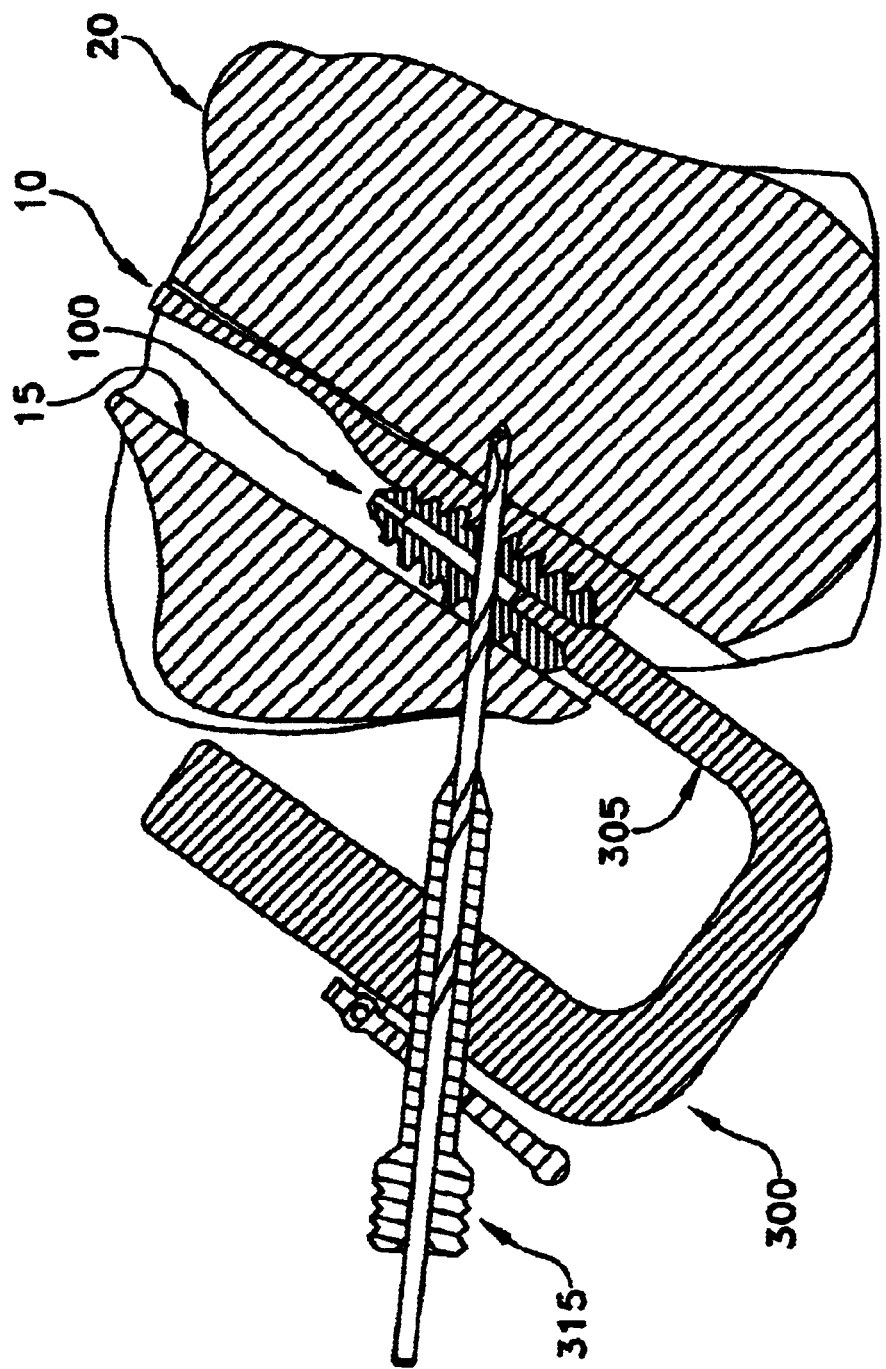
FIGS. 15-17 are side elevational views, partially in section, showing various steps in an alternative method for attaching a graft ligament to a bone.
Figure 16:
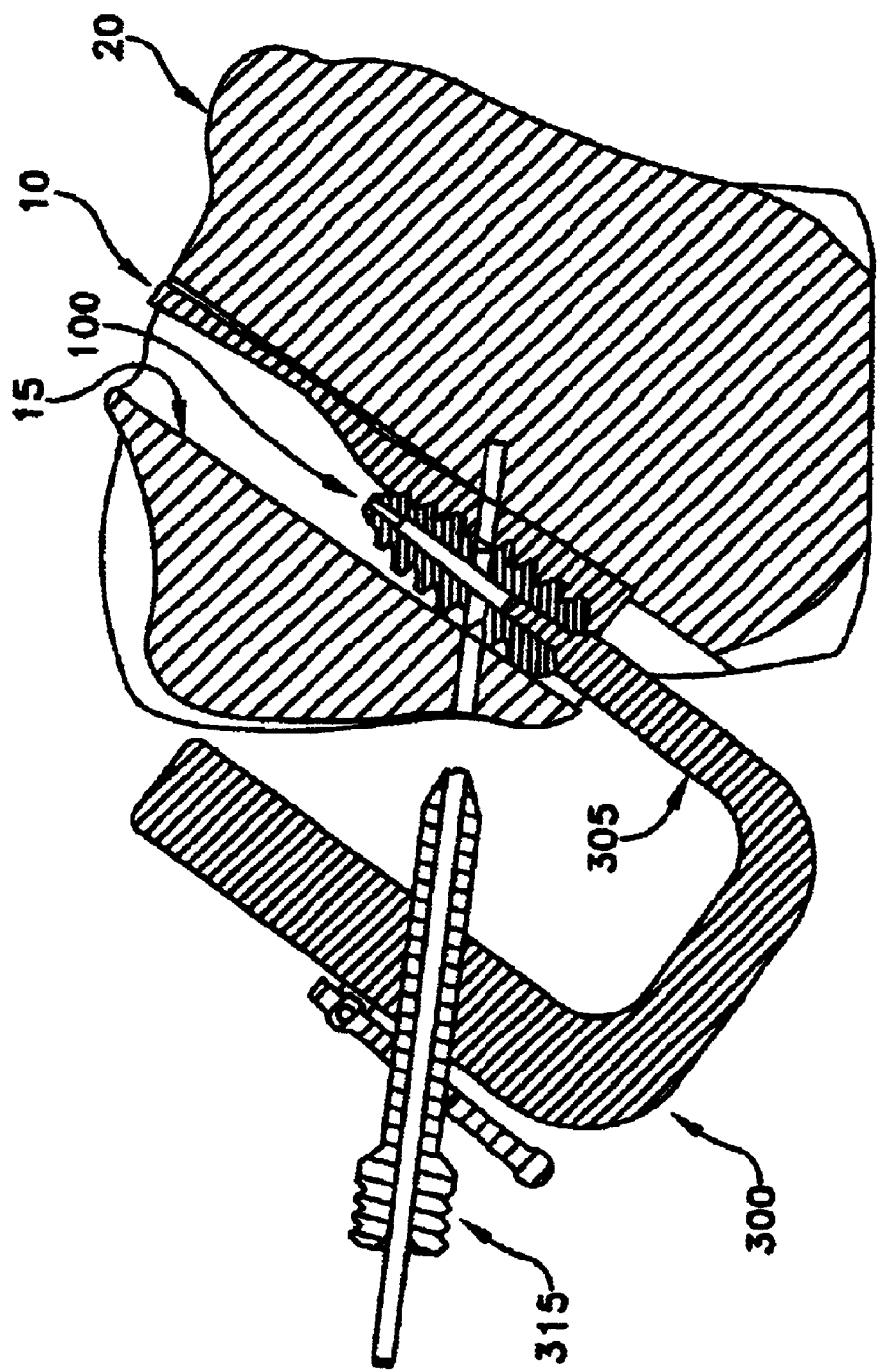
Figure 17:
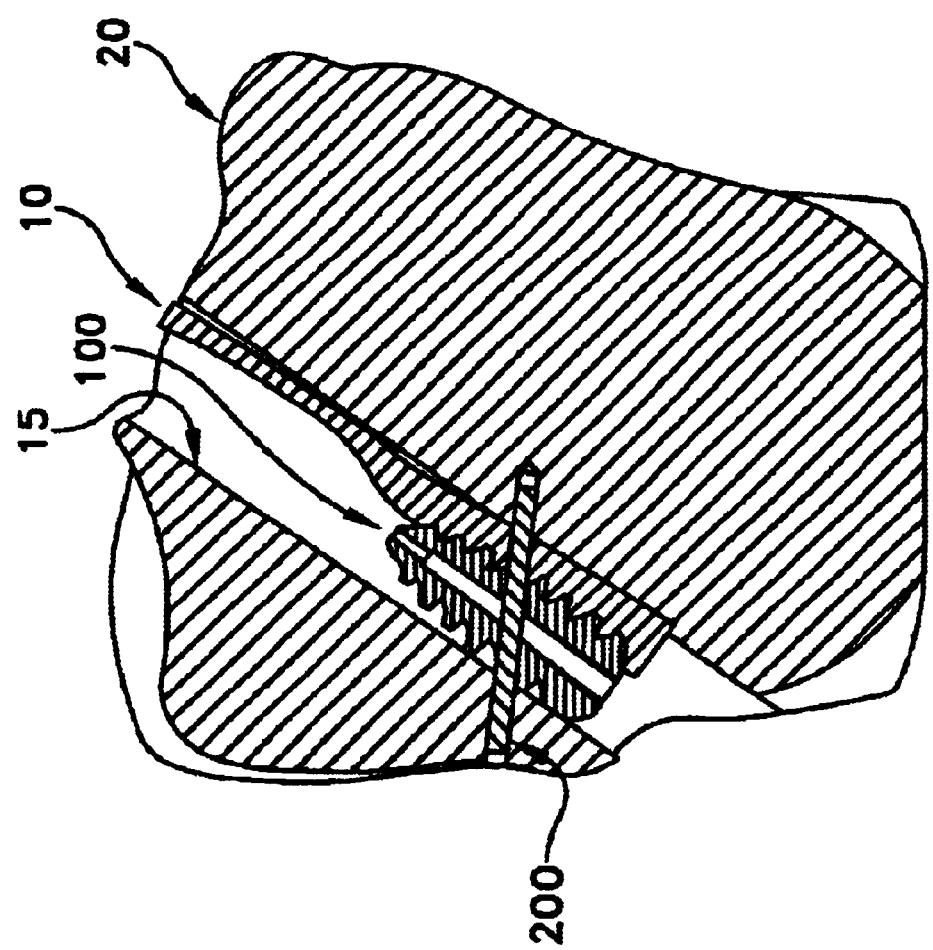

It is also possible to configure transverse guide assembly 300 so that guide member 315 approaches interference screw 100 at an angle other than perpendicular. See, for example, FIGS. 15-17, where guide member 315 approaches interference screw 100 at a acute angle.

Figure 18:
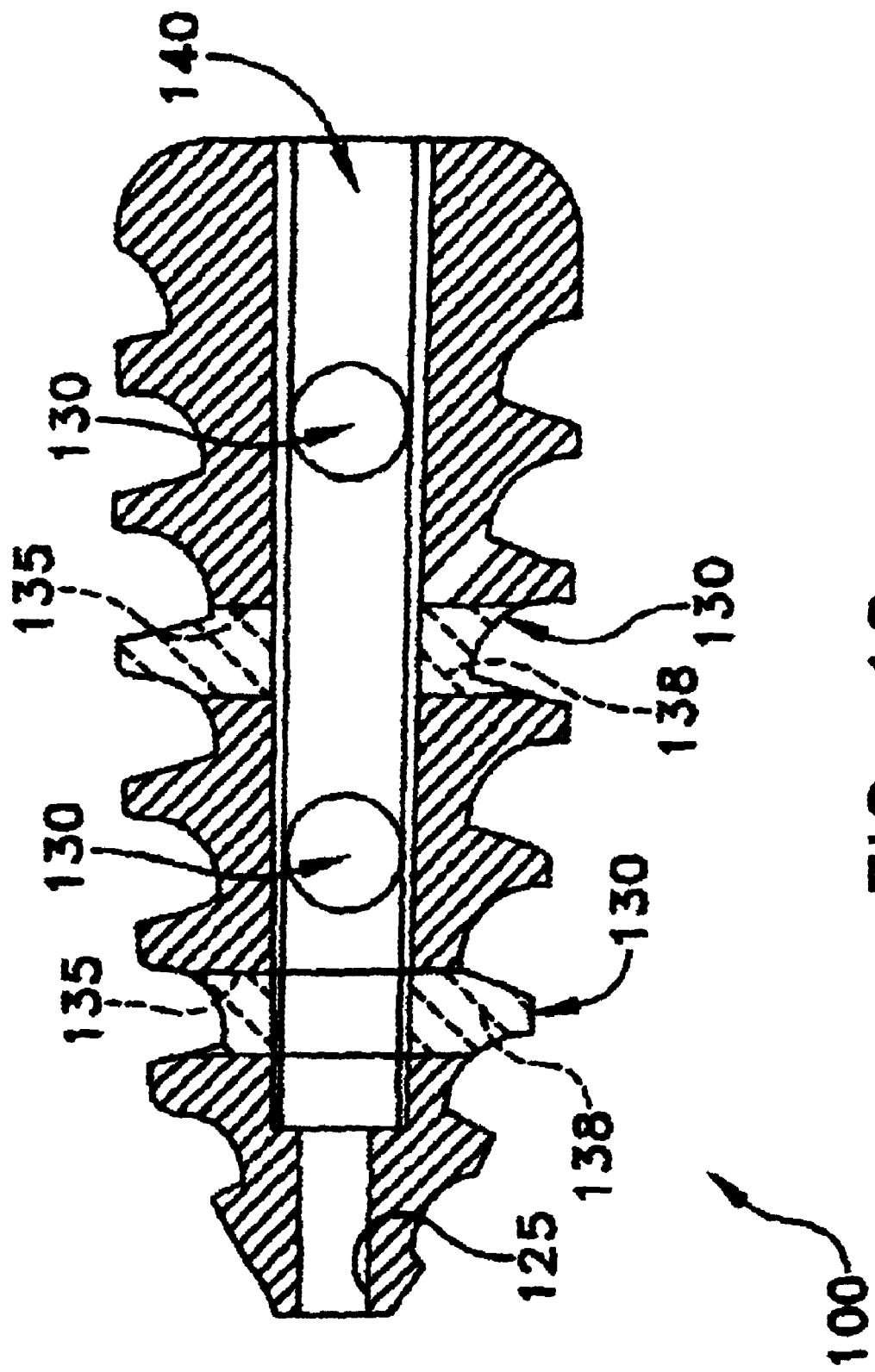
FIG. 18 is a side elevational view of an alternative form of interference screw formed in accordance with the present invention.

It should also be appreciated that, if desired, a plurality of transversely-extending regions 130 may be provided in interference screw 100. Where a plurality of transversely-extending regions 130 are provided, the regions may be spaced from one another about the circumference of the interference screw, or about the longitudinal axis of the interference screw, or both. See, for example, FIG. 18.

In addition to the foregoing, second portion 345 of boom member 310 may permit multiple positions for guide member 315. This construction is advantageous, for example, in situations where interference screw 100 comprises multiple transversely-extending regions 130, whereby one or more transverse pins 200 may be passed through the interference screw at various locations.

It should be appreciated that fixation system 5 may be used in conjunction with a graft ligament 10 comprising a synthetic or harvested graft ligament. Furthermore, where graft ligament 10 comprises a harvested graft ligament, the graft ligament may consist entirely of soft tissue or it may comprise one or more bone blocks as well.

Furthermore, while in the foregoing discussion bone 20 was described as being the tibia, it could also, in the case of an ACL repair, comprise the femur.

Additionally, it should be appreciated that the present invention may be used to reconstruct ligaments other than the ACL. Thus, the present invention could be used to reconstruct the posterior cruciate ligament (i.e., the PCL) or a ligament in the elbow, etc.

Figure 19:
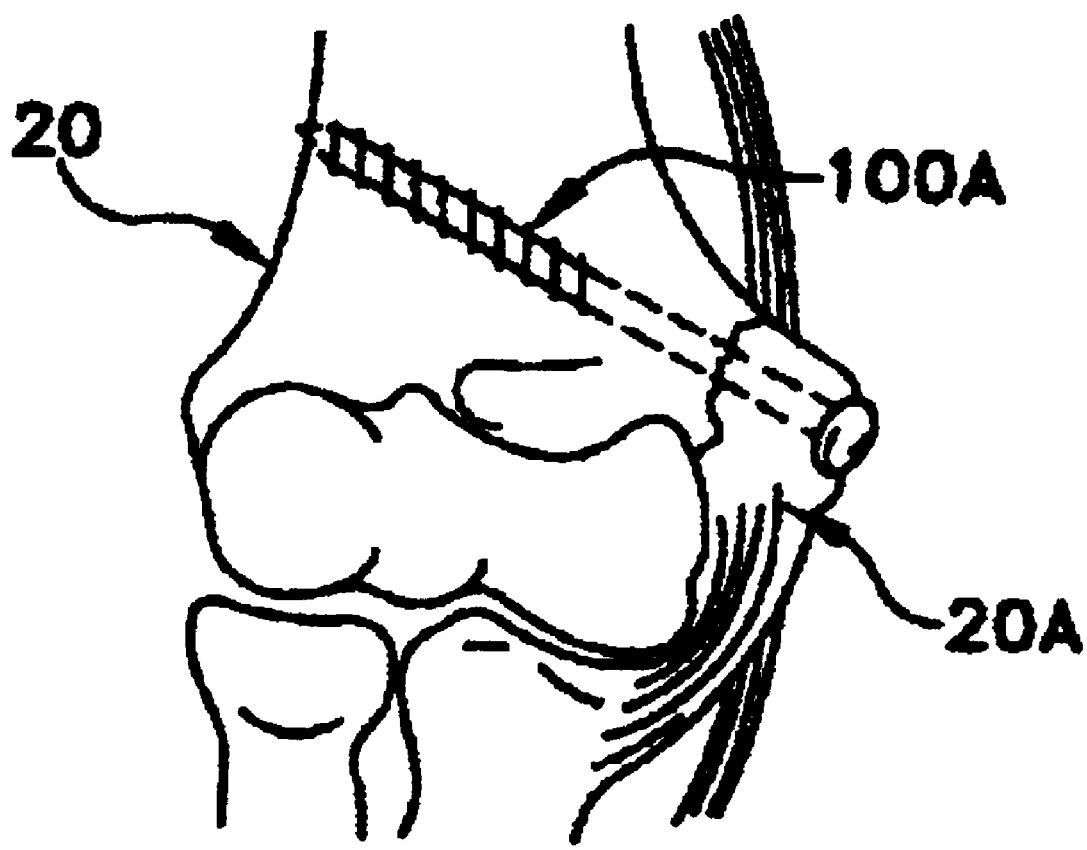
FIGS. 19-21 are schematic views showing various ways for effecting fracture fixation using bone screws.
Figure 20:
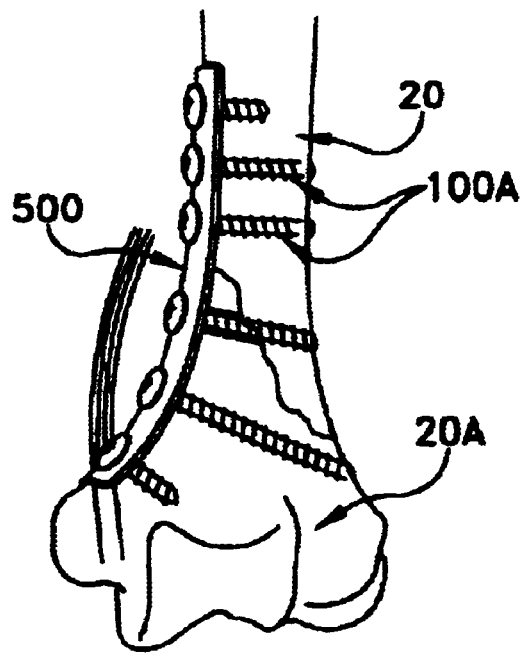
Figure 21:
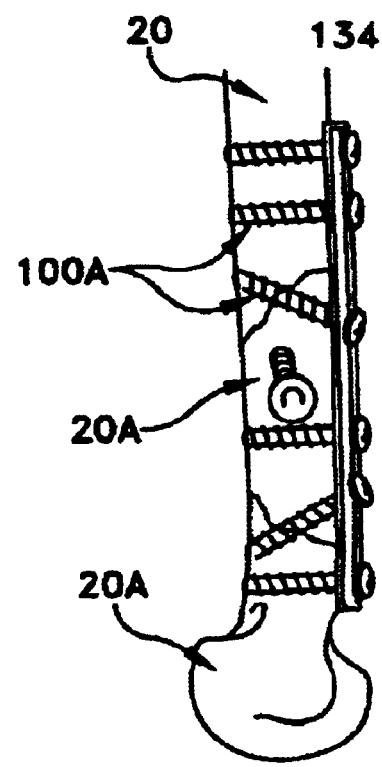

It has also been discovered that is it possible to extend the foregoing concepts to orthopedic screws other than interference screws. More particularly, bone fractures are frequently repaired using bone screws and using bone plates and bone screws. See, for example, FIG. 19, which shows a bone screw 100A securing a bone fragment 20A to a bone 20; FIG. 20, which shows a bone plate 500 and a plurality of bone screws 100A securing a bone fragment 20A to a bone 20; and FIG. 21, which shows a bone plate 500 and a plurality of bone screws 100A securing a plurality of bone fragments 20A to a bone 20.

Bone screws are available in many configurations. They may have deep threads for cancellous bone (i.e., cancellous screws), or shallow threads for cortical bone (i.e., cortical screws). They may be solid or cannulated; and may comprise fully threaded or lag screws (i.e., screws having threads on the distal end thereof, with a smooth shaft between the threads and the head).

In accordance with the present invention, and looking now at FIG. 22, there is shown a bone screw 100A formed in accordance with the present invention. Bone screw 100A comprises a bone screw of the sort known in the art, except that it incorporates at least one transversely-extending region 130 of the sort previously described, and has a transverse pin 200 passed therethrough in accordance with the present invention. Preferably bone screw 100 also includes a keyway 140 of the sort previously described, so that transverse pin 200 can be placed using a transverse guide assembly 300. A transverse pin 200 placed through bone screw 100A provides greater axial and torsional fixation strength for the screw in a bone fragment when compared to a bone screw alone. This greater fixation strength is particularly advantageous in comminuted fractures, where enhanced stabilization of the various fragments will lead to a higher probability of union (i.e., bone healing) and less instability at the fracture site during the healing process.

Having thus described preferred embodiments of the invention with reference to the accompanying drawings, it is to be understood that the embodiments shown herein are provided by way of example only, and that various changes and modifications may be effected by one skilled in the art without departing from the scope or spirit of the invention as defined in the claims.

The invention claimed is:

1. A fixation system for fixing an object to a bone tunnel, the fixation system comprising:
a transverse guide assembly;
a bone screw, wherein the bone screw is adapted to engage both the object and the bone tunnel, the bone screw comprising:
a body having a distal end and a proximal end and a central lumen extending longitudinally along the entire length of the body, wherein the proximal end comprises a keyway, screw threads extending longitudinally along the body, and a transversely-extending region formed in the body, wherein the keyway comprises an angular orientation relative to and aligned with the transverse-extending region; and
a transverse pin, wherein the transversely-extending region is formed for receiving the transverse pin therein, wherein the pin is headless and resides entirely within a transversely-extending tunnel, wherein the a transversely-extending tunnel is aligned with the transverse-extending region.

2. A system according to claim 1 wherein said transversely-extending region comprises a hole formed in the body of the bone screw.

3. A system according to claim 1 wherein said transversely-extending region comprises a bioabsorbable material.

4. A system according to claim 1 wherein said bone screw comprises a plurality of transversely-extending regions.

5. A system according to claim 4 wherein said transversely-extending regions are spaced from one another about the circumference of the bone screw.

6. A system according to claim 4 wherein said transversely-extending regions are spaced from one another about the longitudinal axis of the bone screw.

7. A system according to claim 1 wherein the proximal end of the body of the bone screw has a keyway formed therein so as to permit (i) driving of the bone screw, and (ii) association with the transverse guide assembly for placing the transverse pin through the host bone and through the transversely-extending region formed in the bone screw, whereby to securely lock the bone screw, and hence the object, to the bone.

8. A fixation system for fixing a graft ligament in a bone tunnel, the fixation system comprising:
a transverse guide assembly;
an interference screw wherein the interference screw is adapted to engage both the graft ligament and the bone tunnel, the interference screw comprising:
a body having a distal end and a proximal end and a central lumen extending longitudinally along the entire length of the body, wherein the proximal end comprises a keyway, screw threads extending longitudinally along the body, and a transversely-extending region formed in the body, wherein the keyway comprises an angular orientation relative to and aligned with the transverse-extending region; and
a transverse pin, wherein the transversely-extending region is formed for receiving the transverse pin therein, wherein the pin is headless and resides entirely within a transversely-extending tunnel, wherein the a transversely-extending tunnel is aligned with the transverse-extending region.

9. A system according to claim 8 wherein said transversely-extending region comprises a hole formed in the body of the interference screw.

10. A system according to claim 8 wherein said transversely-extending region comprises a bioabsorbable material.

11. A system according to claim 8 wherein said interference screw comprises a plurality of transversely-extending regions.

12. A system according to claim 11 wherein said transversely-extending regions are spaced from one another about the circumference of the interference screw.

13. A system according to claim 11 wherein said transversely-extending regions are spaced from one another about the longitudinal axis of the interference screw.

14. A system according to claim 8 wherein the proximal end of the body of the interference screw has a-keyway formed therein so as to permit (i) driving of the interference screw, and (ii) association with the transverse guide assembly for placing the transverse pin through the host bone and through the transversely-extending region formed in the interference screw, whereby to securely lock the interference screw, and hence the graft ligament, to the bone.

* * * * *